US008427181B2

(12) United States Patent
Chetelat et al.

(10) Patent No.: US 8,427,181 B2
(45) Date of Patent: Apr. 23, 2013

(54) FLOATING FRONT-END AMPLIFIER AND ONE-WIRE MEASURING DEVICES

(75) Inventors: Olivier Chetelat, Hauterive (CH); Josep Sola I Caros, Neuchatel (CH)

(73) Assignee: CSEM Centre Suisse d' Electronique et de Microtechnique SA—Recherche et Developpement, Neuchatel (CH)

( * ) Notice: Subject to any disclaimer, the term of this patent is extended or adjusted under 35 U.S.C. 154(b) by 443 days.

(21) Appl. No.: 12/919,018

(22) PCT Filed: Mar. 10, 2009

(86) PCT No.: PCT/EP2009/052793
§ 371 (c)(1),
(2), (4) Date: Aug. 24, 2010

(87) PCT Pub. No.: WO2009/112494
PCT Pub. Date: Sep. 17, 2009

(65) Prior Publication Data
US 2011/0001497 A1  Jan. 6, 2011

(30) Foreign Application Priority Data

Mar. 11, 2008  (EP) ..................................... 08152557

(51) Int. Cl.
*G01R 27/08* (2006.01)
(52) U.S. Cl.
USPC ........... 324/692; 324/347; 324/348; 324/444; 324/688; 600/544; 600/545; 600/546; 600/547; 607/45; 607/46; 607/62
(58) Field of Classification Search ................. 324/347, 324/348, 444, 688, 692; 600/544–547, 509; 607/40–46, 62
See application file for complete search history.

(56) References Cited

U.S. PATENT DOCUMENTS

| 3,880,146 | A | * | 4/1975 | Everett et al. ................. 600/523 |
| 4,751,471 | A | | 6/1988 | Dunseath, Jr. |
| 6,292,690 | B1 | * | 9/2001 | Petrucelli et al. ............. 600/547 |

(Continued)

FOREIGN PATENT DOCUMENTS

DE  102004039291 A1  3/2006

OTHER PUBLICATIONS

International Search Report, Dated May 27, 2009 in PCT/EP2009/052793.

(Continued)

*Primary Examiner* — Huy Q Phan
*Assistant Examiner* — Thang Le
(74) *Attorney, Agent, or Firm* — Young & Thompson

(57) ABSTRACT

A follower amplifier with power supply biased by a controlled voltage source such that the power supply potentials are, for the frequencies of interest, as close as possible to the potential of the follower output. There is proposed a front-end electronic circuit for biopotential and impedance measurements with outstanding performances (very high input impedance and gain very close to unity). Preferably, the explicit guard electrode and the explicit electronic unit at the belt are no longer necessary; all electronics is embedded in units placed directly at the measurement sites. Moreover, the proposed front-end electronic circuit allows a drastic simplification of the cabling and connectors since all units are connected to only one wire (the theoretical minimum) for potential reference and current return. Preferably, this wire does not even require an electrical isolation and can be easily embedded in the textile of a shirt, in a garment, mesh, belt, etc.

30 Claims, 19 Drawing Sheets

U.S. PATENT DOCUMENTS

| | | | | |
|---|---|---|---|---|
| 8,086,300 B2* | 12/2011 | Herlerkson | | 600/509 |
| 2002/0026112 A1 | 2/2002 | Nissila et al. | | |
| 2002/0045836 A1* | 4/2002 | Alkawwas | | 600/509 |
| 2004/0210148 A1* | 10/2004 | Van Ess | | 600/509 |
| 2005/0182338 A1* | 8/2005 | Huiku | | 600/544 |
| 2007/0276278 A1 | 11/2007 | Coyle et al. | | |

OTHER PUBLICATIONS

Written Opinion of International Searching Authority, Dated Sep. 14, 2010, in PCT/EP2009/052793.

International Search Report, dated May 27, 2009, from corresponding PCT application.

European Search Report, dated Aug. 22, 2008, from corresponding European application.

Michael A Coyle et al., "Evaluation of an ambulatory system for the quantification of cough frequency in patients with chronic obstructive pulmonary disease", Cough, Aug. 4, 2005, p. 1-7.

Sergio Matos et al., "Detection of Cough Signals in Continuous Audio Recordings Using Hidden Markov Models", IEEE Transactions on Biomedical Engineering, vol. 53, No. 6, Jun. 2006, p. 1078-1083.

Jaclyn Smith, "Ambulatory methods for recording cough", Pulmonary Pharmacology & Therapeutics, 2007, vol. 20, p. 313-318.

J.A. Smith, Cough: "Assessment and Equipment", The Buyers' Guide to Respiratory Care Products, 2006, p. 96-101.

* cited by examiner 12-lead ECG system
lead I:  $V_L - V_R$
lead II:  $V_F - V_R$
lead III:  $V_F - V_L$
augmented lead $aV_R$:  1.5 $V_R$
augmented lead $aV_L$:  1.5 $V_L$
augmented lead $aV_F$:  1.5 $V_F$
precordial leads:  $V_1$ to $V_6$

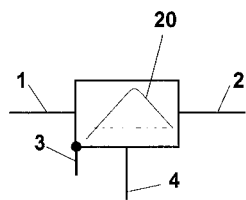
Figure 4
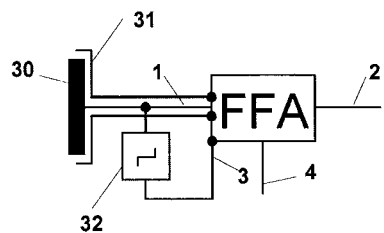
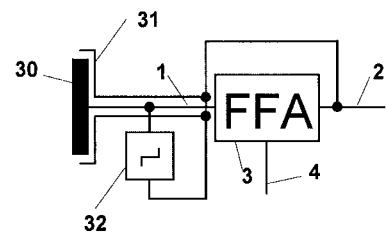
Figure 5 (a)
Figure 5 (b)
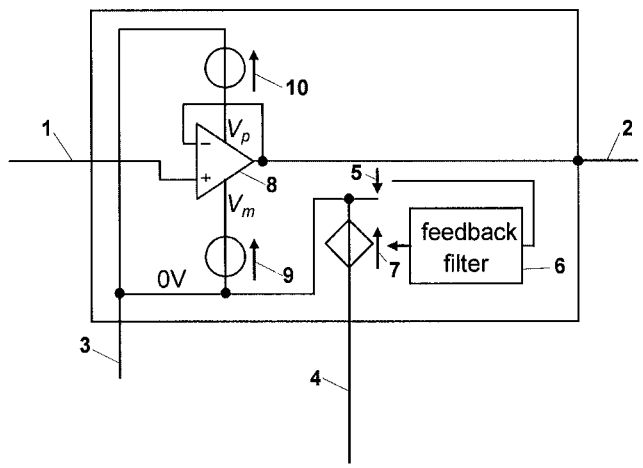
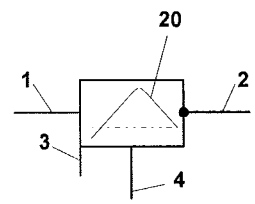
Figure 6 (a)
Figure 6 (b)

side view    top view

FLOATING FRONT-END AMPLIFIER AND ONE-WIRE MEASURING DEVICES

FIELD OF THE INVENTION

The present invention relates to a floating front-end amplifier and to one-wire measuring devices.

BACKGROUND OF THE INVENTION

One-wire measuring devices may be used especially in the field of monitoring vital signs and parameters from biopotentials (e.g. ECG) or/and from impedance measurements (e.g. respiration).

Biopotentials provide information on some electrical physiological process of the human or animal body. Electrodes are used at the interface of the measuring device and the body. Usually, the electrodes are applied on the skin, but they can be elsewhere. They can also be needle electrodes inserted in the body.

The interface between the body and the electrodes is generally a chemical cell that translates ionic current into metallic current. A gel is usually used between the electrodes and the body in order to decrease the contact impedance and consequently the noise and motion artefacts. However, some measuring devices use dry electrodes. Furthermore, some electrodes are totally isolated and only displacement (AC) currents are picked up.

Typical biopotentials are ECG (or EKG), i.e., electrocardiography. Others include for instance EEG (electroencephalography), EOG (electro-oculography), EMG (electromyography), etc. FIG. 1 shows a 12-lead Mason-Likar ECG system. The left side of the figure indicates the placement of the adhesive electrodes and the right side shows a typical schematic diagram of the front-end electronic circuitry used to serve the affixed electrodes.

Electronic circuitry is usually located separately from the electrodes: either in a small recorder at the belt (Holter's system) or in a bed-side box. However, especially for EEG (weak signal) or for isolated electrodes (very high impedance), part of the electronic system may be located at the electrodes in order to keep the noise as low as possible. Such electrodes are called 'active electrodes'.

In FIG. 1, the electrode potentials are buffered by operational amplifiers connected as followers, i.e., with unitary gains. These followers give high input impedance and low output impedance.

The electrode cables are shielded. The shield is optimal when driven by the output voltage of the follower. On the one hand, this protects from capacitive coupling of disturbances, and on the other hand, if the gain g of the follower is exactly unity, it limits the input impedance to the amplifier input impedance. In the real world, the CMRR (common mode rejection ratio) of the follower operational amplifier is not infinite, which means that g is not exactly unity. This results in incomplete cancellation of the parasitic shunt capacitance $C_p$ between the electrode wire and its shield; the capacitance is actually reduced to $C_p(1-g)$, i.e., equal to 0 only if g is exactly unity.

The potential measured at the three electrodes R, L, and F is averaged to the so-called Wilson's central terminal W by three resistances. This potential is set equal to the electronics ground (i.e. to 0V) using a feedback filter and a so-called guard drive electrode G (sometimes also called 'right leg drive electrode'). The transfer function of a typical feedback filter is an integrator with a sign inversion, i.e., $-1/s\tau$, where s is the Laplace variable and $\tau$ the time constant corresponding to the closed-loop frequency. The other electrodes, i.e., $V_1$ to $V_6$, measure, with respect to the Wilson terminal W, the so-called precordial leads.

The input impedance of the measuring device through electrode G is very low and allows the mains disturbance current—originating from capacitive coupling between the body and the measuring device—to preferably flow through electrode G rather than through the measurement electrodes. This way, the mains influence on the biopotential measurement is minimized.

The ECG electrodes are usually disposable, adhesive gel electrodes applied directly at the appropriate place by a doctor or a trained nurse. The electrodes are then connected to wires (one different wire for each electrode). The wires are connected to a recorder, which is a small electronic unit usually placed at the belt. The wires are sometimes attached to the body with tape straps in a way chosen by the doctor or the trained nurse, so as to minimize the risk that the wire weight displaces an electrode and to maximize the subject comfort.

Electrodes are also used in impedance measurement, such as for instance impedance plethysmography, impedance cardiography, body composition impedance, impedance tomography, skin impedance, etc. Impedances are usually measured at high frequency (relative to body frequencies), typically 50 kHz. In order to separate the high impedance at the electrode/body interface from the low impedance of the inner body tissues, a 4-wire scheme such as depicted in FIG. 2 is usually used. In this figure, the impedance Z which is to be measured, and the four interface impedances are drawn in hashed line. Two electrodes are connected to a current source i, while two other electrodes for voltage measurement ($V_2$-$V_1$) are connected to the front-end amplifiers.

To limit as much as possible the discomfort brought by any measuring device, it is advantageous to reduce as far as possible the number of interfaces with the body. In particular, it is of interest to share electrodes for biopotential and impedance measurements whenever this is possible. Furthermore, the guard drive electrode, the electronics unit and the cables can be justified for technical reasons, but are a significant source of obtrusiveness and discomfort for the subject.

Objective non-supervised assessment of cough remains a main challenge in long-term ambulatory data-collection systems.

Standard developments relay either on the digital recording of cough sounds, the analysis of chest wall EMG signals or a combination of both (Smith, "Ambulatory methods for recording cough", Pulmonary Pharmacology & therapeutics 20 (2007) 313-318). Methods based on the analysis of the cough acoustic signal have been reported to provide sensitivity values of 82% (true positive detections over true positive detections and false negative detections). The main reason for such low performances is the inter-subject variability of cough sounds acoustic properties as well as the dependency to transducer placement and configuration. Ambient noise might be an additional important source of false positive detections. (Matos et al., "Detection of cough signals in continuous audio recordings using Hidden Markov Models", IEEE Transactions Biomedical Engineerings, 2006; 53:1078-83).

Among some new developments appeared in the last few years, one must cite the efforts recently performed with the Vivometric Lifeshirt (Coyle et al., "Evaluation of an ambulatory system for the quantification of cough frequency in patients with chronic obtrusive pulmonary disease", Cough 2005). The authors used the LifeShirt to record Respiratory Inductance Plethysmography (RIP), acoustic sounds, electrocardiogram and accelerometry and reported sensitivity values of 97% (Smith, "Cough: assessment and equipment", The Buyers Guide to Respiratory Care Products, 2007). The detailed description of the method is given in a Vivometric's patent (Coyle et al. "Systems and methods for monitoring cough", US200710276278).

The main purpose of the invention is to propose a front-end electronic circuit for biopotential and impedance measurements with outstanding performances (very high input impedance and gain very close to unity). In a preferred embodiment, the explicit guard electrode and the explicit electronic unit at the belt are no longer necessary; all electronics is embedded in units placed directly at the measurement sites. Moreover, the proposed front-end electronic circuit allows a drastic simplification of the cabling and connectors since all units are connected to only one wire (the theoretical minimum) for potential reference and current return. In a preferred embodiment, this wire does not even require an electrical isolation and can be embedded in the textile of a shirt, in a garment, mesh, belt, etc.

SUMMARY OF THE INVENTION

According to a main characteristic, the present invention relates to a follower amplifier with power supply biased by a voltage source controlled by the output of a feedback filter fed by the voltage between the follower output potential and the power supply potentials.

In other words, one can also say that the follower amplifier is powered by a positive and negative floating power supplies connected together to an internal ground. To avoid undetermined potentials, a controlled voltage source sets the internal ground potential with respect to the potential of an external ground. Note that, in its principle, it does not matter to have both positive and negative power supplies with the same magnitude. One of them could even be zero. In this case, the follower amplifier would work in single-supply operation.

Further characteristics comprise:
The feedback filter is preferably chosen in such a way that its input is controlled to zero for the frequencies of interest. In other words, the follower power supply potentials are, for the frequencies of interest, as close as possible to the potential of the follower output. Two positive effects results from this. First, the negative effect of a too-low follower input impedance is considerably reduced since the voltage on this impedance is drastically reduced in the frequencies of interest (ideally to zero). Second, the real gain of the follower (which is in practice close to, but not equal to unity) matters less when the input voltage is close to zero (ideally equal to zero), since zero times whatever results to zero. Therefore, the effective follower gain is closer to unity when powered by floating power supplies following the output of the follower.

The feedback filter can be advantageously built with an operational amplifier either a) powered by the same power supply as the follower and driving the external ground, or b) powered by its own power supplies and driving the internal ground.

The floating power supplies by definition are free to float with respect to other power supplies. In other words, the potential between them is undetermined, like if there would be no galvanic connection. Batteries are perfect for floating power supplies.

Galvanically isolated DC/DC converters (for instance through modulation—isolated transformer—rectifier, or through charge pumps) are also examples of floating power supplies.

To get the best performances, the floating front-end amplifier must be shielded. The shield can be driven by the internal ground potential or, even better, by the follower output.

It is also important to shield the input line of the floating front-end amplifier by the internal ground potential or, even better, by the follower output. Doing so will drastically reduce the effect of any stray capacitance or impedance, thus leading to outstanding high impedance.

Any amplifier has a polarization current which has to be conducted to ground. Special circuitry is required when this current cannot naturally flow through the voltage source to measure, like, for instance, when a capacitance is inserted in series. A solution is to conduct the current through a resistance between the input and the internal ground. Thanks to the property of the invention described above, this resistance does not significantly alter the input impedance. Applying the classical approach to the invention (see FIG. 8b) results into outstanding performance that can be advantageously exploited, for instance, in the use of isolated electrodes.

Overvoltage protection circuits also constitute an additional input load that can be significant for very high input impedance requirements. By connecting the overvoltage protection circuit to the internal ground will virtually increase the effective parasitic impedance of the overvoltage protection circuit (for the same reasons as described above).

The present invention also concerns one-wire devices for biopotential and/or impedance measurements of a body comprising a plurality of units connected to the same external wire used for potential reference and/or for current return. No other wire connects the units. This one-wire approach results in simplified cabling and connectors. Instead of a physical wire, one can also connect the units by contact directly to a conductive shirt, garment, mesh, belt, etc.

At least, one unit has to be a reference unit, the other being measuring units. However, units can be built in such a way that they can switch, at start-up or during operation, from the 'reference unit' function to the 'measuring unit' function.

The reference unit, thanks to the use of a floating front-end amplifier with its input connected to a so-called reference electrode and its external ground connected to a so-called guard electrode, make sure that the potential of the external wire connecting the units is the same than the one inside the body (below the reference electrode). This has several significant advantages.

First, for biopotential measurements, there is no mains disturbance (50 Hz or 60 Hz) on the external wire. Note that there would be a significant mains disturbance if the external wire were directly connected to the reference electrode without a floating front-end amplifier and a guard electrode). In order to cope with this disturbance, the prior-art solutions would be to use an additional electrode (sometimes actively controlled like the electrode G in FIG. 1). This additional electrode would be used as ground for instrumentation amplifiers with high common mode rejection. This is the classical way to solve the mains disturbance problem. When the additional electrode mentioned above is actively controlled (like in FIG. 1), it is called a guard electrode. The invention also has a guard electrode in the reference unit, but its purpose is different. In FIG. 1, one observes that several electrodes are required to drive the guard electrode, because the prior-art goal is to minimize the common mode disturbances for the instrumentation amplifiers (not shown in FIG. 1). However, several electrodes require several wires, which is definitely not a one-wire solution. Moreover, if one can imagine placing the guard electrode in the vicinity of a single measuring electrode, this is impossible for several electrodes. In the invention, only one electrode (the reference electrode) is used to drive the guard electrode, because its goal is to serve the external ground of the floating front-end amplifier. Furthermore, there is no longer any problem to have the guard electrode at the vicinity of the reference electrode. In the invention, the reference unit, as well as all measuring units, are directly at measuring locations.

Second, for impedance measurements, the high impedance at the interface between the electrode and the inside of the body is virtually reduced to zero and any injected current can freely flow. If the external wire was directly connected to the reference electrode without using the floating front-end amplifier and the guard electrode, the outer skin layer and the interface of the electrode would make a high impedance, and a significant voltage would be needed on this impedance to let any current flow through it.

Third, as the potential inside the body is the same as the one of the external wire, the effect of stray capacitance between the external wire and the body is virtually cancelled. This is true especially at the reference unit. For other body locations, while the injected current flows through the body impedance, a small voltage will be created between the inside of the body and the external wire. However, this voltage is very low compared to what it would be if there were only one electrode and no floating front-end amplifier. Note that a classical four-wire solution for impedance measurement (FIG. 2) would require (at least) two external wires, one of which with a potential significantly higher than the inside of the body in order to be able to inject the measuring current through the high-impedance of both the outer skin layer and the interface with the electrode (especially for isolated electrodes). Moreover, the external wire may be without electrical isolation. Remember that the voltage with the inside of the body is low. In addition the impedance of the outer layer of the skin and the impedance of the interface between the skin and the external wire are high. A low voltage on high impedance makes, as a mater of fact, the electrical isolation.

Fourth, as there is only one external wire, there is no risk of crosstalk between wires.

Finally, as the external wire does not need a shield (contrary to some of the prior-art solutions), its movement does not modify its capacitive load and no motion artefacts can originate from the motion of the external wire.

Each of the measuring units has means to measure the voltage between a so-called biopotential/impedance electrode and the external wire. For biopotential measurements, this voltage is directly the biopotential voltage between the measuring and reference unit locations.

For impedance measurements and for this voltage to be to different from zero, an additional so-called injection electrode is needed for at least one of the measuring units. In addition, there must be in the measuring units with an injection electrode a current source or other means to circulate a current through the injection electrode, the body, the guard electrode of the reference unit and back by the external wire. When the current source is not set to zero, a current will flow through the body and a voltage drop (between the impedance electrode and the external wire) will be measured by all measuring units. The current source may, for example, produce an alternative current with constant magnitude and frequency outside the bandwidth of any biopotential, so that there would be an easy way to extract and separate the voltage components originating from bioelectric activity and from the current injection.

As the current is the same at any time in a current loop, an appropriate modulation of the current source can be used to transmit to the reference electrode synchronization information. For example, one can image a sine-wave current synchronizing, in frequency and phase, an oscillator in the reference unit. This is especially interesting when the function of reference unit is taken in turn by the other units during operation. This way, all units may have their own oscillator always kept in phase, which is useful if one wants other measuring units than the one injecting the current to measure the phase of the impedance (its magnitude can be measured even if the units are not synchronized). For less demanding synchronization requirements, one can also imagine that the high-frequency alternative current is modulated by a low frequency square wave. All units can detect this square wave on the measured voltage. Such a square wave may be useful to simultaneously sample all signals, for instance at a given time after the rising edge.

More than one of the measuring units can have a current injection electrode and means to circulate a current through the reference unit. However, the currents have to be modulated in such a way their effect can be distinguished by signal processing. For instance, the current sources can be turned on one at a time in turn, or they can be all on, but with carriers at different frequencies.

Further characteristics are presented hereafter:

The measuring units can also benefit from the outstanding performance brought by the floating front-end amplifier in terms of input impedance and unity gain. In one embodiment, the input of the floating front-end amplifier is connected to the biopotential/impedance electrode and its external ground to the external wire. For measuring units with a current injection electrode, one terminal of the current source is connected to this electrode and the other to the external ground of the floating front-end amplifier.

In another embodiment, the current injection electrode is connected to the external ground of the floating front-end amplifier. The current source is connected between the internal ground of the floating front-end amplifier and the external wire. Note that the current source may be absent (or set to zero) when this embodiment is used for biopotential measurement alone. In this case, it may seem odd to call the second electrode 'current injection electrode', since no current is actually injected. However, this is a particular case.

Biopotential measurements are subject to motion artefacts. One way to reduce their effects is to take into account information regarding the contact impedance of the electrode during the signal processing. With the one-wire devices as described so far, it is easy to add means to measure the contact impedance of the current injection or guard electrode. However, for best results, the contact impedance of the other electrode, i.e, the biopotential/impedance or reference electrode, is preferred. Therefore, the roles of the two electrodes of the units would be preferably swapped for impedance measurement (with respect to their original configuration still used for biopotential measurement). This is rendered possible by switches that physically exchange the connection of the two electrodes with the electronic circuit. For a given time slot, the measurement is performed for biopotentials with the original configuration, and for the next time slot, the measurement is performed for impedance (including contact impedance) with the role of the electrodes swapped.

Another way would be to achieve the exchange of electrodes would be to take advantage of the frequency separation of biopotentials (measured at low frequencies) and impedance (measured at high frequencies). Electrical filters, preferably passive filters with capacitance and inductance, can be used for this.

Among the numerous applications of the invention, one would be the non-supervised assessment of cough with solely chest impedance measurements. Means for this assessment may be added to the one-wire device.

BRIEF DESCRIPTION OF THE DRAWINGS

For a better understanding of the present invention, reference is made to the following description, taken in conjunction with the accompanying drawings, and its scope will be pointed out in the appending claims.

The invention will now be described, by way of example only, with reference to the accompanying drawings, in which:

FIG. 4 depicts the symbol that will be used to represent the floating front-end amplifier in more complex circuits, the characteristic (20), which is the transfer function of the feedback filter, being specific to the application, and the connection to the shield (box around the symbol) with the internal ground (3) being visible by a dot;

FIGS. 5 (a) and 5 (b) depict two embodiments of the floating front-end amplifier connected to an electrode and featuring extended shield and overvoltage protection, first embodiment being based on a connection to the internal ground (3) and second embodiment to a connection to the output (2);

FIGS. 6 (a) and 6 (b) show the embodiment and the symbol of a floating front-end amplifier similar to the one of FIG. 3, but with the shield connected to the output (2);

DETAILED DESCRIPTION

Figure 1:
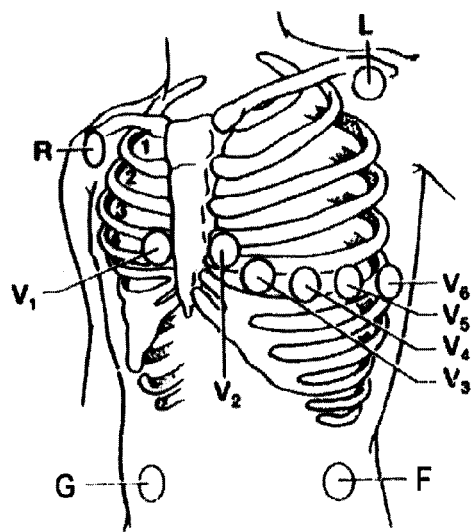
FIG. 1 depicts a schematic drawing of a typical front-end circuit for prior-art ECG apparatus.
Figure 1:
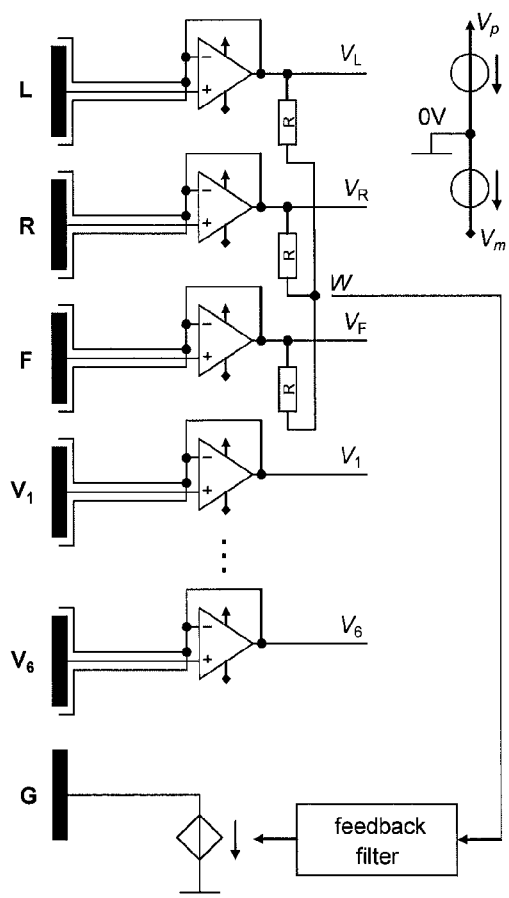
Figure 2:
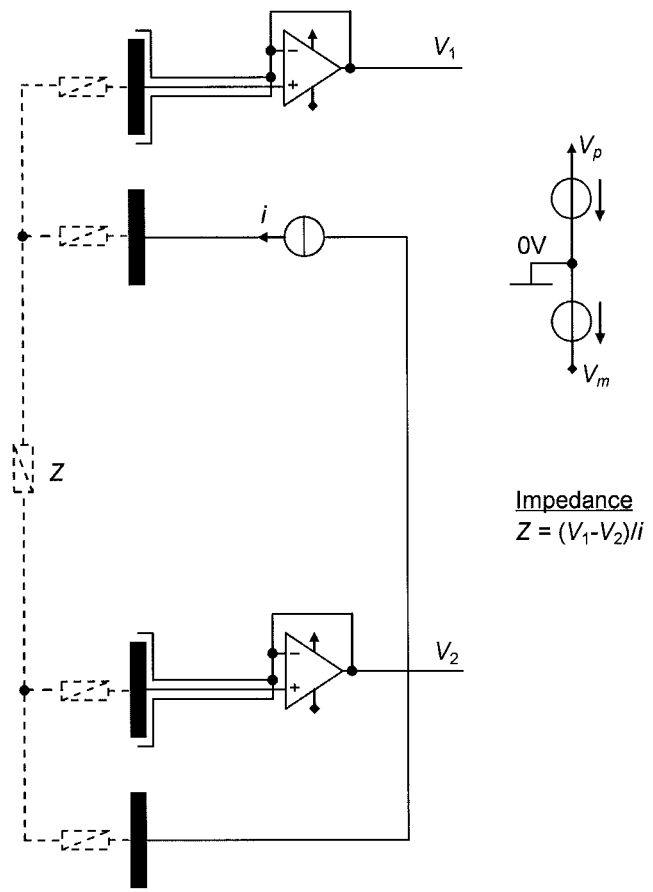
FIG. 2 depicts another prior-art front-end circuit for the measurement of impedance (four-wire scheme)

FIGS. 1 and 2 have been described above. The same reference numerals will now be used for same parts or the like.

Figure 3:
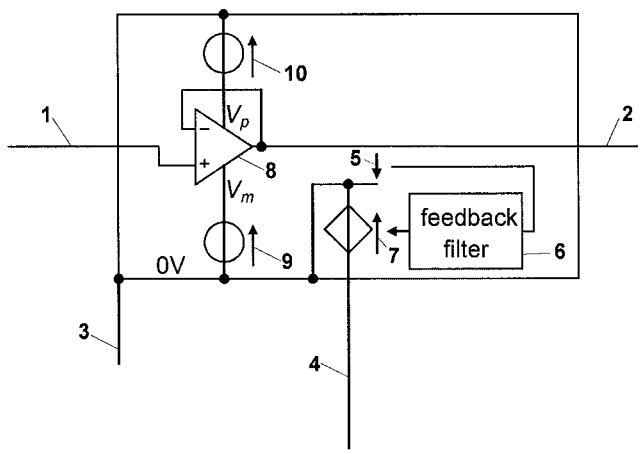
FIG. 3 is a schematic diagram of the front-end circuit proposed in the present invention (floating front-end amplifier) with a shield connected to the internal ground (3)

FIG. 3 shows an embodiment of a floating front-end amplifier, according to the present invention. The input (1) connected to the follower amplifier (8) features very high input impedance, while the output (2) features low output impedance. The potential of the output (2) equals the potential of the input (1) with great accuracy. The potential of the internal ground (3) is actively controlled to the same potential of the input (1).

The voltage (5) between the output (2) and the internal ground (3) can actually be seen as the error signal feeding the controller (6) (or feedback filter) which determines the control voltage (7) so that the potential of the internal ground (3) equals the potential of the input (1) whatever is the potential of the external ground (4).

The potential of the internal ground (3) is also the common to potential of the power supplies (9) and (10) of the operational amplifier (8). This implies that the input impedance $Z_{in}$ of the floating front-end amplifier is much greater than the input impedance $Z_{in\_opa}$ of the operational amplifier (8). As a matter of fact, one has $Z_{in}=(1+h)Z_{in\_opa}$, where h is the gain of the open loop, i.e., of the feedback filter.

The CMRR (common mode rejection ratio) of operational amplifier (8) is very large, but not infinite. This results in a gain of the follower close to, but not exactly equal to one. However, as the feedback filter (6) controls the potential of the internal ground (3) so that it equals the potential of the input (10), the voltage amplified by the operational amplifier (8) is close to 0. Therefore, whatever is the gain g of the follower, the output is close to 0, i.e., equal to the potential of the input (1). This effect implies an effective CMRR much higher than the one of the operational amplifier (8) alone. As a matter of fact, the effective gain is (g+h)/(1+h), where h is the open loop gain.

FIG. 4 shows an abstract view of the floating front-end amplifier. In the middle of the symbol, the transfer function (20) of the feedback filter (6) is displayed, because this function may vary with the application. When the function is not explicit, the letters FFA (Floating Front-end Amplifier) are displayed instead. The dot recalls to what terminal the shield around the amplifier is connected, which is, in this embodiment, to the internal ground (3).

FIGS. 5 (a) and 5 (b) show two embodiments of the floating front-end amplifier connected to an electrode (30). In the first embodiment shown in FIG. 5 (a) the electrode (30) and its wire to the input (1) are shielded. The potential of the shield (31) is the same as the potential of the internal ground (3). The overvoltage protection (32)—for example, two ordinary to diodes in parallel and top to bottom—is connected from the wire (1) to the internal ground (3). As the potential of the internal ground (3) is controlled to the potential of the input (1), the impedance of the overvoltage protection is amplified by 1+h, where h is the gain of the feedback filter.

In the second embodiment shown in FIG. 5 (b), the potential of the shield (31) is the same as the potential of the output (2). The properties of the second embodiment depend only on the bandwidth of the follower (8). The performance of the second embodiment is identical to that of the first embodiment when h is infinite and therefore, in terms of performance, the second embodiment is better. However, the shielding implementation may be easier in the first embodiment. A mix of both embodiments is also possible, for instance, having the wire and electrode shield (31) connected to the output (2) and the overvoltage protection (32) to the internal ground (3), or the other way around. From now on, only the second embodiment will be used in the description, but it should be understood that the other embodiments are also possible. Moreover, the overvoltage protection (32) will be omitted for the sake of simplicity of the description.

Except for some wire openings, it is preferable that the internal ground (3) shields all the components of the floating front-end amplifier. In the same idea as described above, another embodiment is to envelop all the components of the floating front-end amplifier by a shield connected to output (2) as shown in FIGS. 6 (a) and 6 (b). In this case, the connection dot in the symbol is shown at the output (2) as depicted in FIG. 6 (b). In theory, this latter variant is slightly better, but in practice, one may want to use the same PCB (Printed Circuit Board) plane for shielding and power supply. In this case, the first embodiment is preferable. In the sequel, only this first embodiment will be used, but it should be understood that the other one is possible too.

Figure 7:
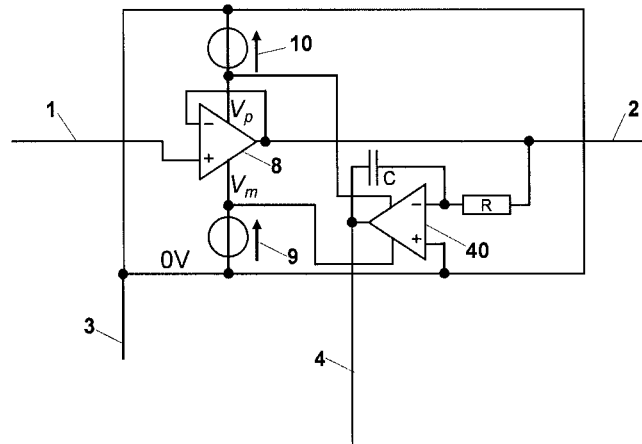
FIGS. 7 (a) and 7 (b) show the embodiment and the symbol of a floating front-end amplifier with integrator as feedback filter.
Figure 7:
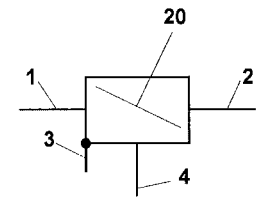

FIG. 7 (a) depicts an implementation of a typical feedback filter (6) of transfer function (20) equal to −1/RCs, as symbolized in FIG. 7 (b). This implementation requires only one operational amplifier (40), which must be powered by the two voltage sources (9) and (10) of the follower (8) so that the otherwise floating potential of the internal ground (3) is correctly set with respect to the potential of the external ground (4). The circuit realising the feedback filter is a classical inverting integrator with a resistance R and a capacitance C connected to the negative input of the operational amplifier.

Figure 8:
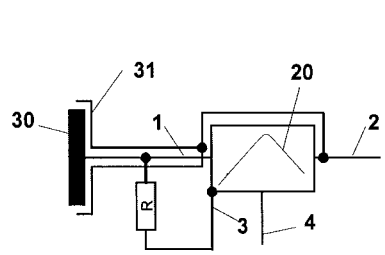
FIGS. 8 (a) and 8 (b) are two others embodiments of a floating front-end amplifier connected to an electrode and featuring an extended shield, a feedback filter transfer function with zero gain at frequency zero, and circuits to shunt the polarization current of the follower amplifier.
Figure 8:
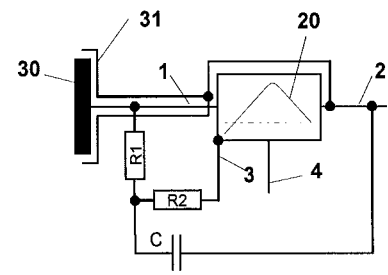

As the gain h of feedback filter (6) is infinite for the zero frequency (DC), the input impedance of the floating front-end amplifier is infinite at this frequency. Therefore, in an application like the one of FIGS. 5 (a) or 5 (b), the (tiny but not null) polarization current of the follower (8) must flow to the body through electrode (30). This is not a very serious problem, except for the purely capacitive coupling of isolated electrodes. In this case, FIGS. 8 (a) and 8 (b) depict two solutions. In the first one, the resistance R is used to shunt the polarization current. The influence of this resistance R is kept low for frequencies in the bandwidth of the feedback filter (20), since for these frequencies, the effective resistance is R(1+h), where h is the gain of the feedback filter. The second solution combines the effect of the first one with the classical approach that uses the resistances $R_1$, $R_2$ and the capacitance C. However, the resistance $R_2$ is connected to the internal ground (3)—the classical solution would rather be equivalent to the connection to the external ground (4).

Figure 9:
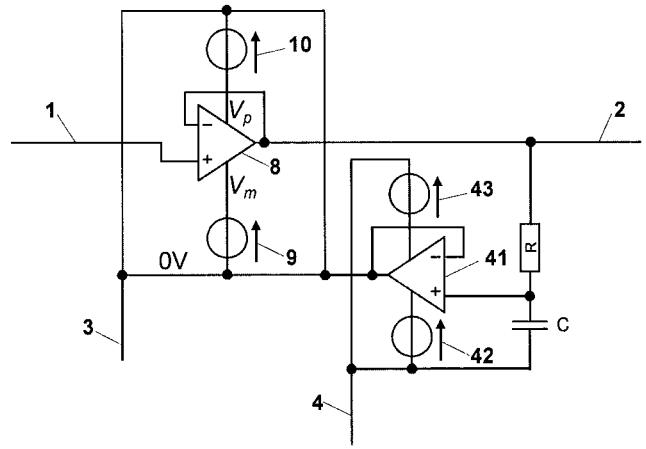
FIG. 9 shows an alternative to FIG. 7 (a) for the construction of the floating front-end amplifier, in particular for the way of powering the operational amplifier used by the feedback filter.

FIG. 9 shows an alternative to FIG. 7 for the construction to of the floating front-end amplifier. This embodiment uses separate power supplies (43) and (42) for the feedback filter amplifier (41). The power supplies are in direct connection with the external ground (4). This embodiment is sometimes preferable to the other, because in this configuration, the power supplies (9) and (10) can easily be derived from the power supplies (42) and (43). Moreover, the power supplies (42) and (43) of several floating front-end amplifiers can be shared like, for instance, in the configurations of FIG. 16 (in case the units would be powered by the same power supply). In this embodiment, the feedback filter uses a follower (41) and the inverted integrator function of the feedback filter is realised with a passive RC filter at the input of the follower (41). One can check that the voltage (5) between the output (2) and the internal ground (3) results into an inverted integrated voltage (7) between the external ground (4) and the internal ground (3). In the sequel, only the embodiment of FIG. 7 (a) will be used as base for other variations of the transfer function (20). It is however always possible by replacing the resistance R and the capacitance C by other impedances to get the same transfer function (20) for both circuits of FIGS. 7 and 9.

Figure 10:
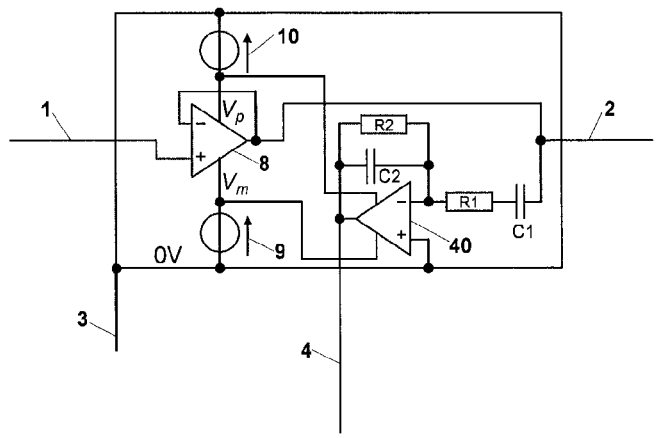
FIGS. 10 (a) and 10 (b) show the embodiment and the symbol of a floating front-end amplifier effective for a specified frequency band.
Figure 10:
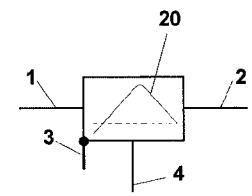

FIG. 10 (a) depicts the implementation of a selected feedback filter (6) with transfer function (20) equal to $-R_2C_1s/(1+R_1C_1s)(1+R_2C_2s)$. This type of transfer function is suitable, for example, for the application of FIG. 8 (a) or 8 (b). The realisation of this transfer function with the resistance $R_1$, $R_2$, the capacitance $C_1$, $C_2$ and an operational amplifier is a classical circuit.

Figure 11:
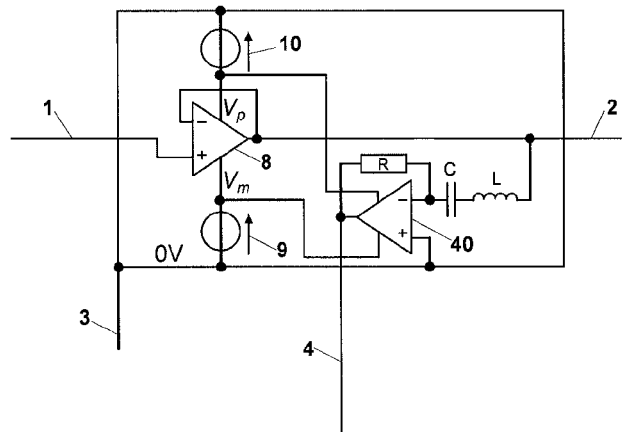
FIGS. 11 (a) and 11 (b) show the embodiment and the symbol of a floating front-end amplifier tuned for a specified frequency.
Figure 11:
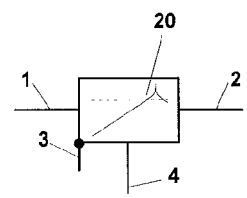

FIG. 11 (a) shows the floating front-end amplifier tuned for a specific frequency $f_0$. At this frequency, the input impedance is to theoretically infinite and the gain of the amplifier exactly one. The transfer function (20) of the feedback filter (6) is $-RCs/(1+LCs^2)$. In addition, one has the following equation:

$$f_0 = \frac{1}{2\pi}\sqrt{\frac{1}{LC}}$$

Figure 12:
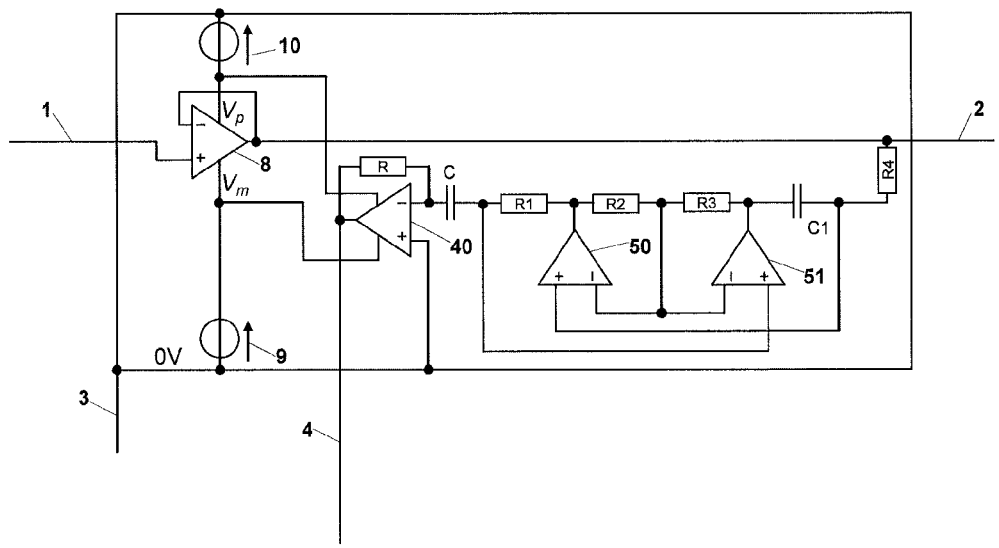
FIG. 12 depicts another embodiment of a floating front-end amplifier as in FIG. 11 (a) but with simulated inductance.

FIG. 12 depicts a floating front-end amplifier identical to the one of FIG. 11 except for the fact that the inductance is simulated with a classical circuit comprising two operational amplifiers (50) and (51) and four resistances $R_1$, $R_2$, $R_3$, $R_4$ and one capacitance C. The inductance L of the feedback filter can be calculated as the product $L=CR_1R_3R_4/R_2$.

Figure 13:
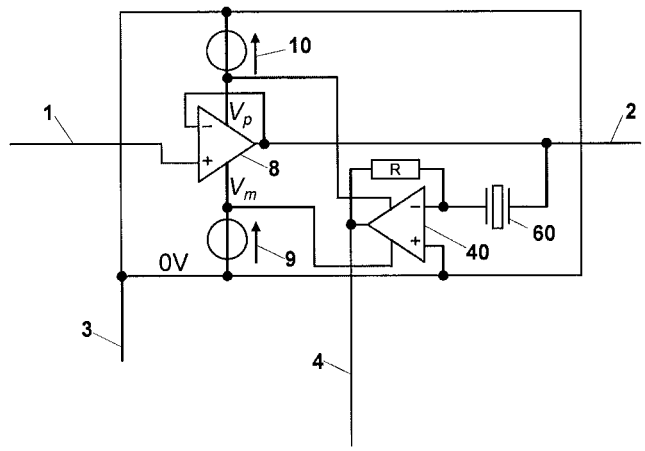
FIG. 13 depicts another embodiment of a floating front-end amplifier as in FIG. 11 (a) but with resonator.

FIG. 13 shows another possibility of avoiding the use of a real coil to implement the floating front-end amplifier of FIG.

11. As a matter of fact, both the coil and the inductance are replaced by an electromechanical resonator (60).

Many other transfer functions are possible for the feedback filter as long as the closed loop is stable and that the open loop gain is sufficient at the frequencies of interest. In particular, any sum of the transfer functions presented so far may be used (as long as the closed-loop system remains stable).

Figure 14:
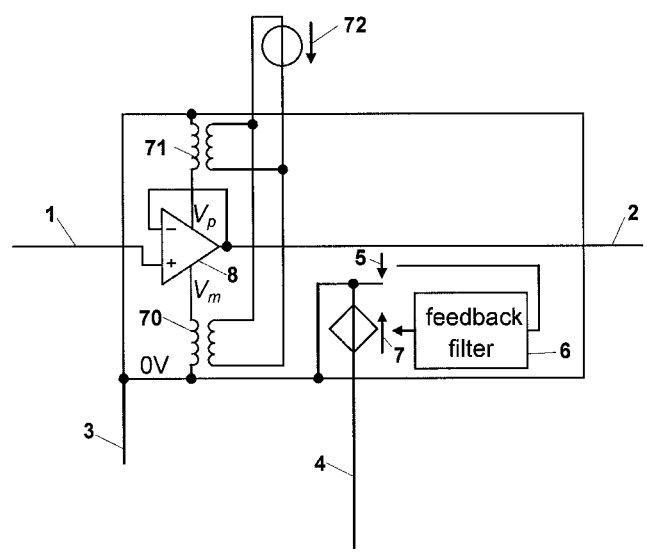
FIG. 14 shows a floating front-end amplifier powered by ideal transformers connected to a fixed power supply.

The power supplies (9) and (10) of the floating front-end amplifiers described so far are floating voltage sources, i.e., with no galvanic link with other voltage sources that may be used for other functions. Moreover, each floating front-end amplifier must have its own power supplies (9) and (10) with no galvanic link with the others. Batteries may be a possible solution, but it is sometimes preferable to use a general power supply (72) and DC/DC transformers (70) and (71) as depicted in FIG. 14.

Figure 15:
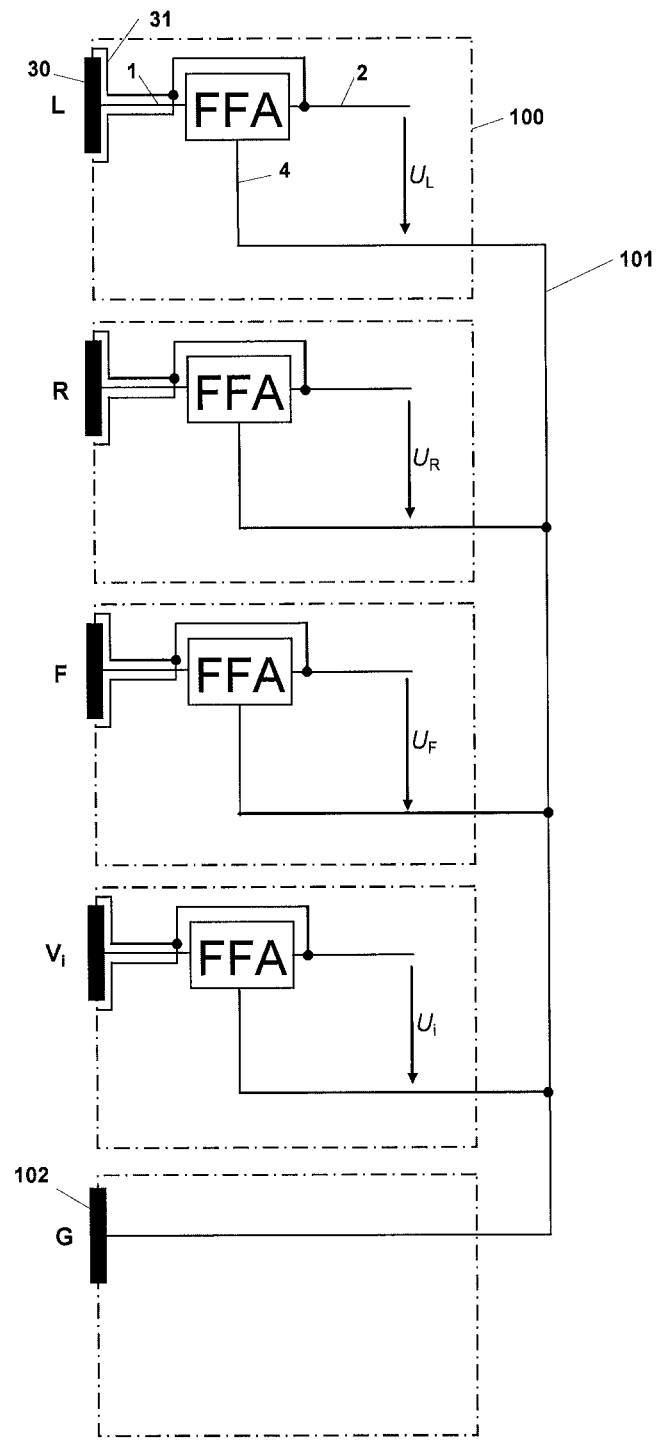
FIG. 15 shows a one-wire measuring device for biopotential measurement with injudicious reference unit.

FIG. 15 shows a possible embodiment of a one-wire measuring device for biopotential measurement. In this configuration, floating front-end amplifiers are used within units (100) connected together by a single wire (101). This wire is also connected to a guard electrode G (102) as reference potential. Each measuring units comprises an electrode connected to a floating front-end amplifier. As it will be the case from now on, the particular embodiment of the floating front-end amplifiers chosen in the one-wire measuring device embodiments is not important; any floating front-end amplifier embodiment may be used according to the desired performances. Moreover, to be useful, the one-wire measuring devices must comprise means to measure and process the voltages carrying the information. As in this patent the focus is onto the front-end electronics, such means are often omitted in the drawings like in FIG. 15.

The configuration of FIG. 15 is simple but not recommended, because the voltages $U_L$, $U_R$, $U_F$, and $U_i$ are highly polluted by the mains disturbance. Supposing that the voltages $U_L$, $U_R$, $U_F$, and $U_i$ are available in digital form, one can always calculate differences such as $U_L-U_R$. In theory, this should cancel the so-called 'common mode', but to be effective in practice, the approach requires an ADC (Analogue to Digital Converter) with a large input range and a very accurate translation gain. Moreover, the ADC samplers must be very well synchronized.

Figure 16:
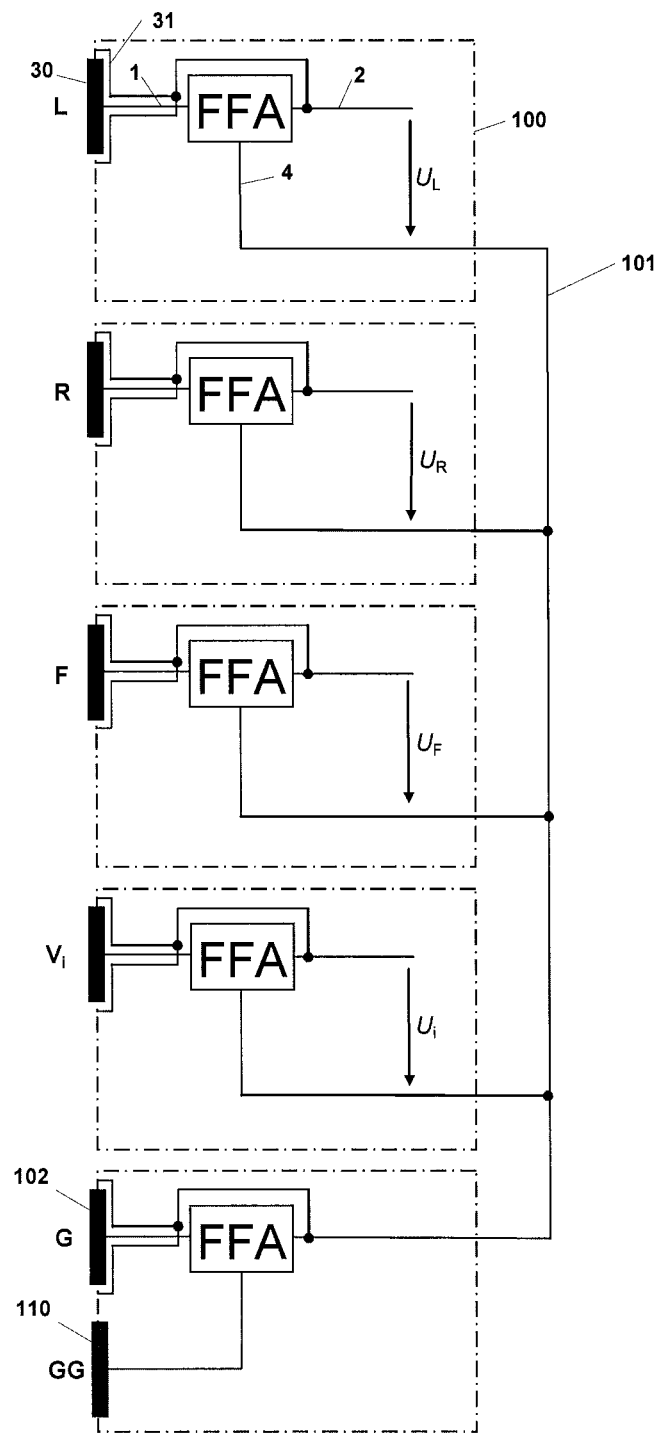
FIG. 16 shows an embodiment of a one-wire measuring device for biopotential measurement with one guard electrode in the reference unit.

A much better solution is to extend the reference electrode G (102) with a guard electrode GG (110) as depicted in FIG. 16. The potential of the wire (101) is now clean from the mains disturbances that are rejected by the feedback filter of the floating front-end amplifier connected to the reference electrode G. In this way, differences such as $U_L-U_R$ are free from mains disturbances. The key point is that there should be a path with low impedance for the mains current flowing by capacitive coupling from the body to the earth through any electrode. It can be seen that for the configuration of FIG. 16, this is indeed the case.

It is also possible to suppress the unit associated with the electrode G and add a guard electrode to any of the measuring electrodes L, R, F, $V_i$ instead. The unit with the guard electrode is named 'reference unit' and the other units 'measuring units'.

Figure 17:
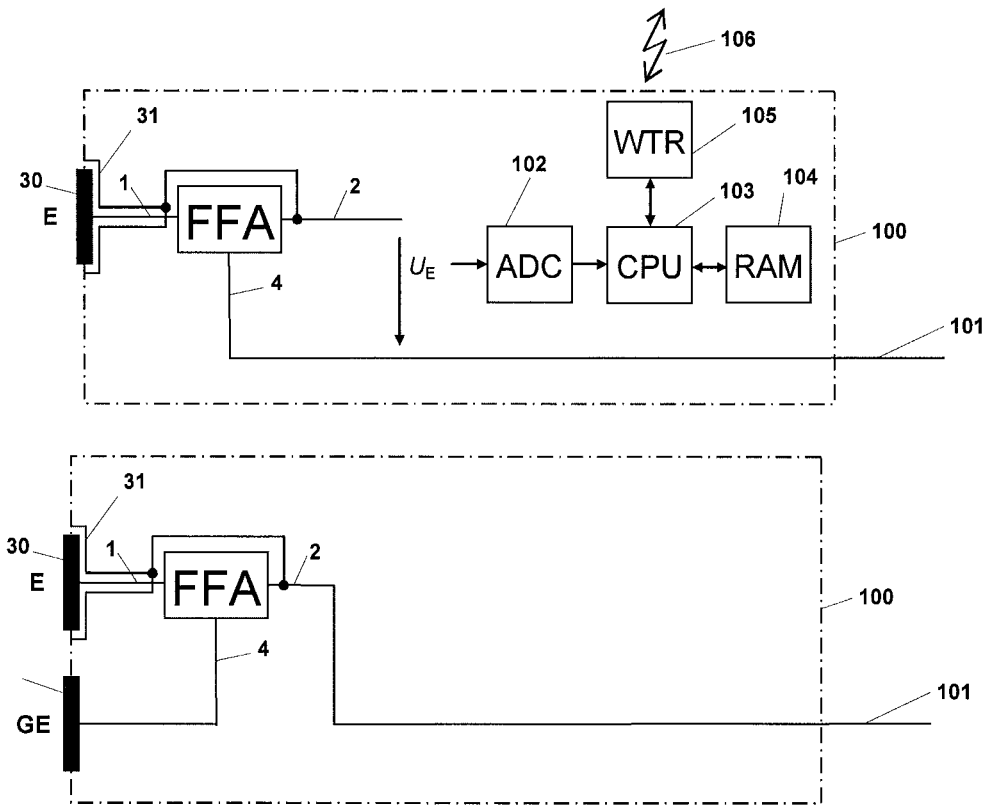
FIG. 17 shows an embodiment of a one-wire measuring device for biopotential measurement comprising a generic measuring unit and a reference unit.

FIG. 17 depicts the diagram of the generic units used. There are two types of unit. The first type (the measuring units) can be duplicated, while the other (the reference unit) is unique in a particular system. All units are connected to the same wire (101). Every unit comprises a floating front-end amplifier, and every measuring unit also contains an ADC (102), a CPU (Central Processing Unit) (103), some memory (104), and a WTR (Wireless Transmitter/Receiver) (105). The ADC, the CPU, the memory (RAM) and even the WTR can be in a single chip, called a microcontroller. The RAM can be used to record the biopotential $U_E$, but this function may be optional in some applications. The WTR may be used for online or offline (recovered from the RAM) transmission of the biopotential $U_E$. A wired (online or offline) transmission through dedicated wires may also be considered in some applications. The synchronization of ADC samplers between units can be achieved using a wireless signal (106). Another method that will be described later (FIG. 27) is to use an electrical signal flowing through the electrodes, the body and the wire (101). For some signals (such as the ECG) and in some applications, one can also accept a known incertitude in the hardware synchronization, because the information of the signal itself (such as the R-wave in the ECG) may be rich enough to allow post-synchronization in software of the signals.

Figure 18:
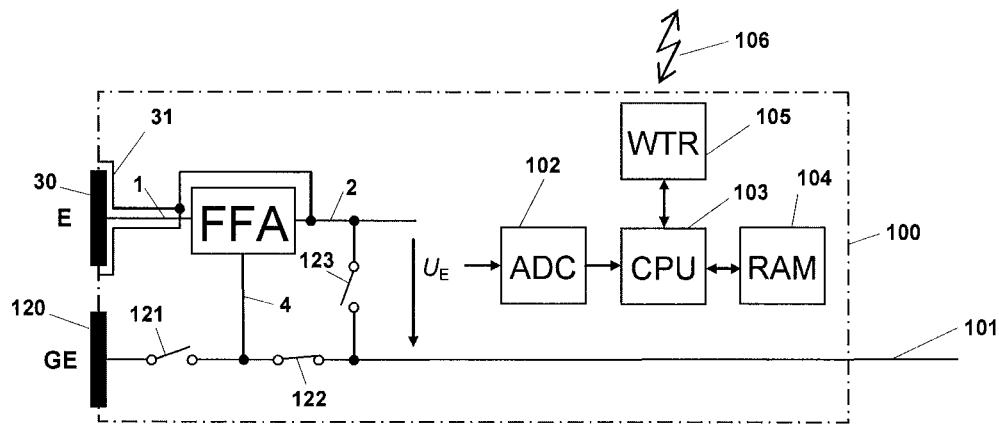
FIG. 18 shows an embodiment of a one-wire measuring device for biopotential measurement with a generic unit that can play either the role of measuring unit or of reference unit.

There is normally only one unit at a time that behaves like reference unit. However, in some applications, it may be advantageous that this role is taken sequentially by all units. In this case, the combined generic unit of FIG. 18 will be used for all units. Each unit comprises three switches that are used to make the unit a measuring or a reference unit. All units but one will have their switches (121) and (123) open and their switch (122) closed.

With the concept of combined generic unit, all units have two electrodes. In this case, a variant to FIG. 17 is to have all units with their switches (121) closed and (122) open, and all units but one (the reference unit) with their switch (123) open. This variant may be preferable, because it is simpler than the other; as two switches are always closed, respectively open, their implementation is trivial.

In FIG. 16, as the signals are processed in each unit (100), there is no need to have an explicit unit for recording, such the one used, for instance, with Holter's recorders.

Figure 19:
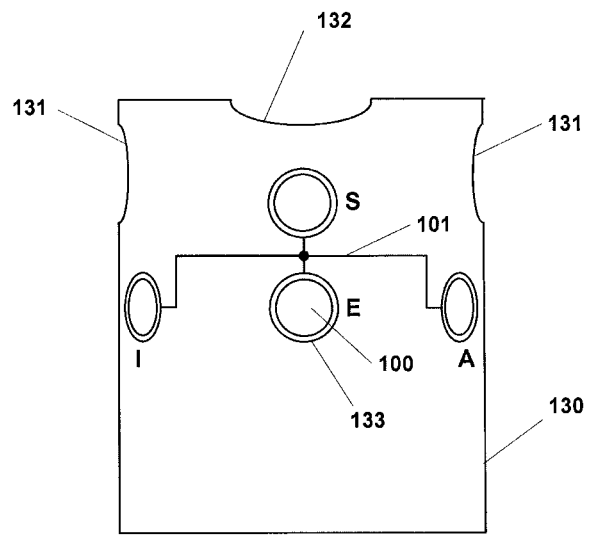
FIGS. 19 and 20 show two arrangements adapted to a one-wire measuring device according to the present invention.

FIG. 19 shows a body garment (130) with collar (132) and openings (131) for arms. This garment is used with the invention to measure an ECG. Note that the EASI system is used in this example. The EASI system is slightly different with respect to the number and placement of electrodes to the one shown in FIG. 1, but this difference is not essential. The explicit guard electrode G, as the one shown in FIG. 1 is no longer needed. The positions of the other electrodes are clearly identified with mounting rings (133). There is no need for specially qualified personnel to correctly place the electrodes. Just putting on the garment will position the electrodes at the right place. The mounting rings are linked by a galvanic connection, which can be a wire or even the garment fabric itself if it is conductive. The units (100) are clipped in mounting rings (133).

Figure 20:
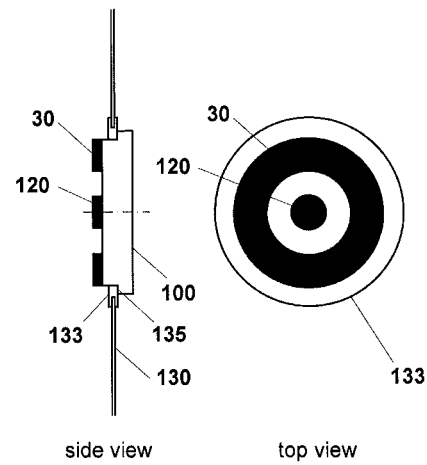

FIG. 20 depicts an example that shows how the galvanic contact (135) between the mounting ring (133) and the unit (100) may be realised when clipped. The clipping mechanism can be based, for instance, on magnetic adhesion, but any other standard way of attaching two mechanical parts together may be used. As there is only one contact, thanks to the one-wire technology presented in the present invention, the connection is trivial and can be made cheap and robust.

FIG. 20 also shows a possible configuration of the biopotential electrode (30) and the guard electrode (120). This configuration is concentric, but of course, many other geometries and arrangements are possible. In principle, the electrodes may also be connected remotely from the housing of unit (100).

Figure 21:
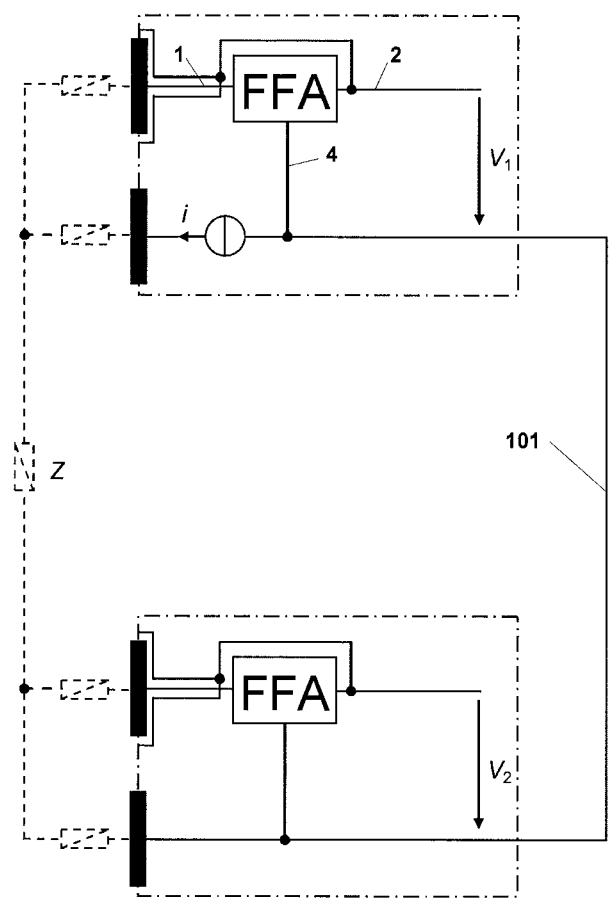
FIG. 21 shows a one-wire measuring device for impedance measurement with injudicious reference unit.

FIG. 21 shows a possible use of the floating front-end amplifier for a one-wire impedance measurement. The impedance Z which is to be measured is drawn in hashed line. Note that the current source i is connected between one electrode and the external ground (4), which is also connected to the external wire (101). However, in another embodiment (see FIG. 22), the external ground (4) is directly connected to the electrode while the current source i is inserted between the internal ground (3) and the external wire (101).

Except for the use of the floating front-end amplifiers that offer outstandingly high input impedance—which is already very appreciable in an impedance measurement as disclosed herein—these configurations are similar to the one of FIG. 2. Unfortunately, this simple scheme suffers from the similar faults as those described for the ECG of FIG. 15. In order to be effective, the approach requires to measure $V_1$ and $V_2$ using exactly the same ADC gain and time base according to an isochronous demodulation scheme. Assuming that these assumptions are fulfilled, the subtraction $V_1-V_2$ can be made numerically after transmission of the data.

Figure 23:
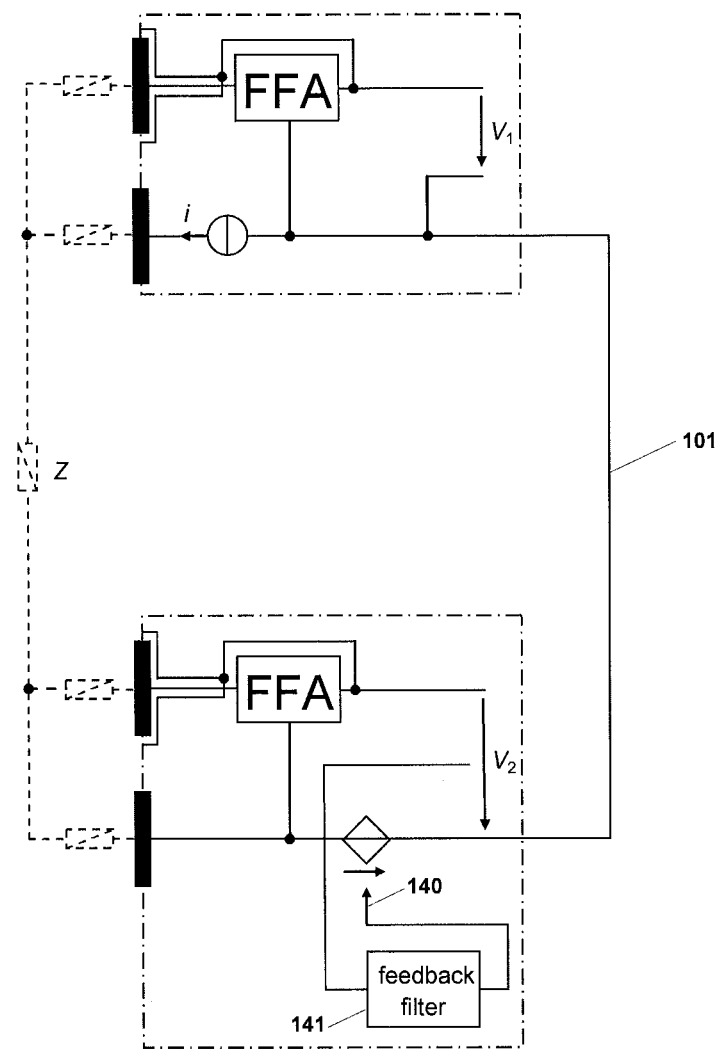
FIG. 23 shows an embodiment of a one-wire measuring device for impedance measurement.

The solution is shown in FIG. 23 where a voltage source (140) is controlled by a feedback filter (141) so that the voltage $V_2$ is zero. The feedback filter is similar to the one described for the floating front-end amplifier. With the voltage $V_2$ equal to zero, one does not require $V_2$ to perform the subtraction $V_1-V_2$, because the result is $V_1-0=V_1$. Moreover, the time base for the demodulation—which should be isochronous with the current sine wave so that the real and imaginary part of the impedance can be measured—is used only in the unit that produces the current. As this information does not have to be transferred to the other unit, there is no longer a problem. This approach also has the advantage of approximately doubling the possible voltage range for the current injection. Another significant advantage is that the voltage between the wire (101) and the inside of the body is much smaller. Therefore, the capacitive coupling between the wire (101) and the inside of the body is reduced to its minimum. In a configuration similar to the one of FIG. 2, this coupling is especially significant for isolated electrodes and for wires close to the skin. Therefore, the principle of FIG. 23 allows more accurate impedance measurements to be made, particularly in difficult configurations.

Figure 24:
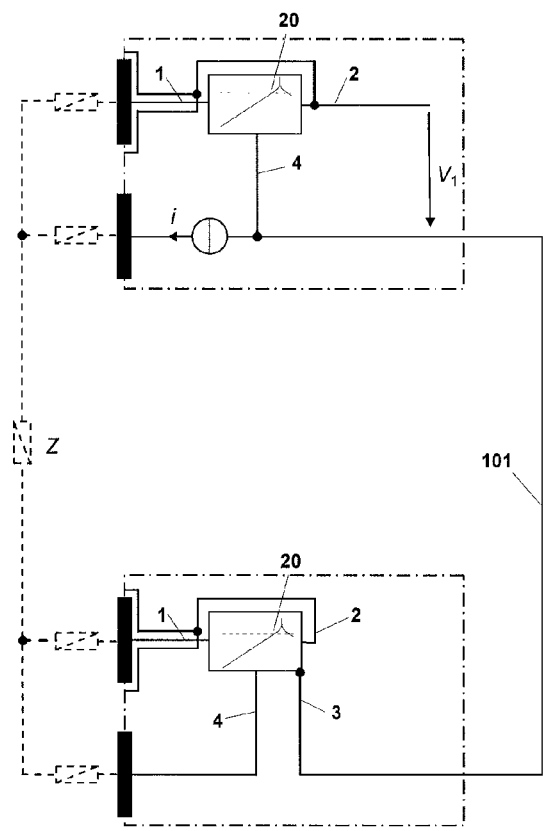
FIGS. 24 (a) and 24 (b) show two other embodiments of a one-wire measuring device for impedance measurement.
Figure 24:
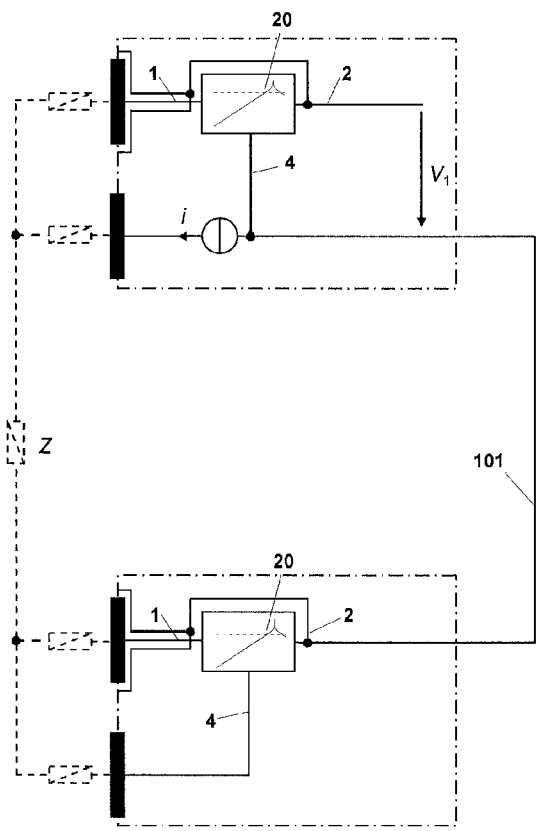

When the feedback filter (141) is identical to the feedback filter of the floating front-end amplifier (6)—which may be acceptable in most applications—the configuration can be simplified to the embodiment shown in FIG. 24 (a). As an example, in FIG. 24 (a), the feedback filter (20) is optimized for a sine wave current injection (e.g., at 50 kHz).

Similarly to the case discussed in reference to FIGS. 5 (a) and 5(b) for the overvoltage protection, another variant is to connect directly the wire between the units to the output (2) instead of the internal ground (3) as depicted in the embodiment of FIG. 24 (b). From now on, only this variant will be considered, because it is generally preferable. However, it is understood that other variants could, as in FIG. 24 (a), also be used instead.

The measuring unit with the current source i can be duplicated in a multi-impedance measuring device. Each current source i may be turned on sequentially or use a different modulation (for example carriers with different frequencies).

Figure 25:
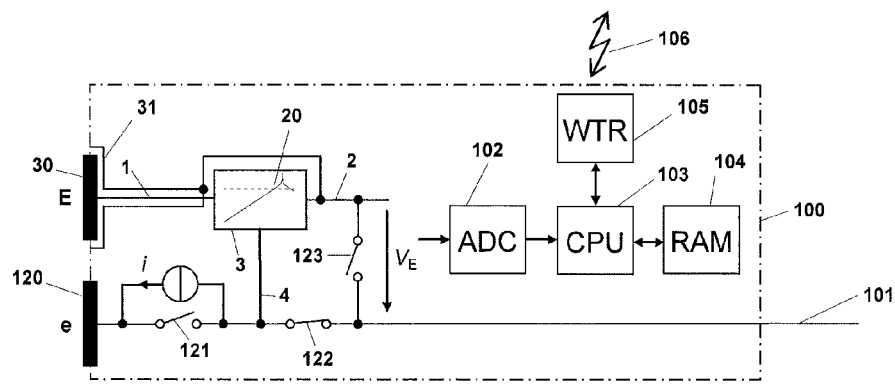
FIGS. 25 and 26 depict two embodiments of combined generic units for a one-wire measuring device for impedance measurement.
Figure 26:
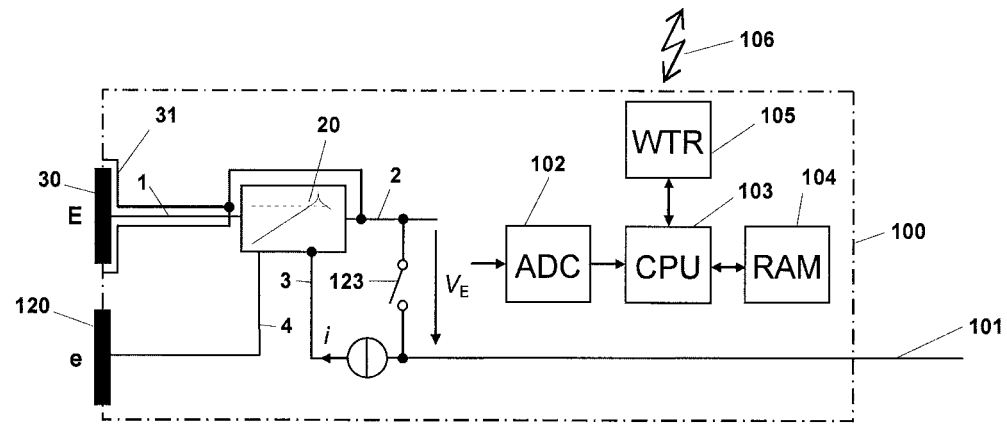

FIG. 25 depicts another embodiment of the present invention with a combined generic unit for impedance measurement. Alternatively, the current source i can be connected as in FIG. 22. In this case, the combined generic unit for impedance measurement is slightly modified as shown in FIG. 26.

Figure 27:
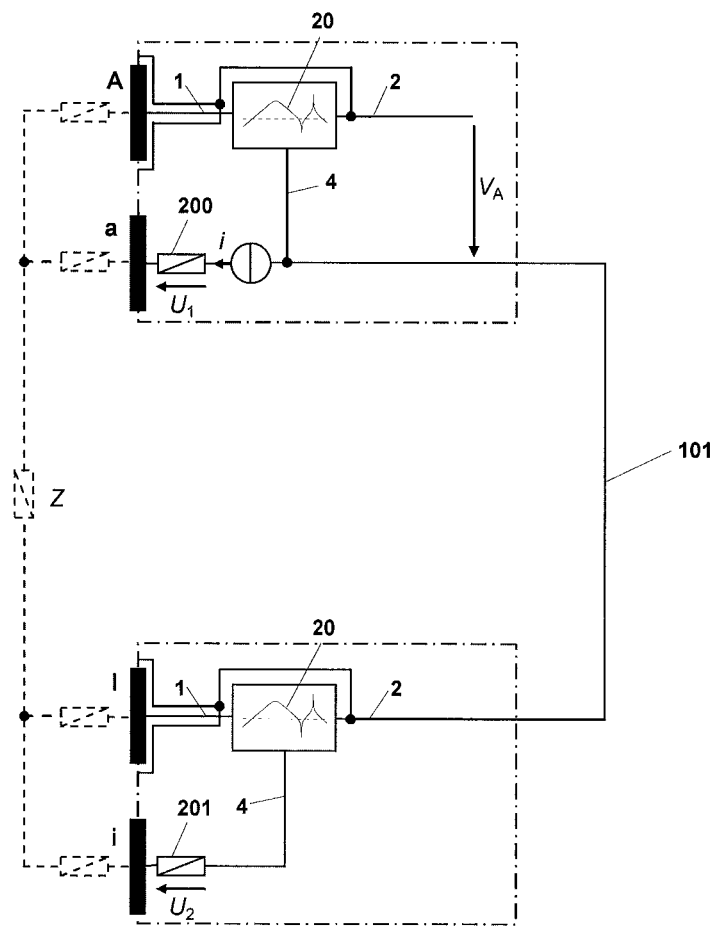
FIGS. 27 to 29 show embodiments for a one-wire measuring device in a configuration for biopotential and impedance measurements.

FIG. 27 shows another embodiment of the present invention for the measurement of both biopotential and impedance through the same electrodes linked by one sole external wire (101). The transfer function (20) of the feedback filter is chosen so that it has a high gain for both the biopotential and impedance frequencies. The voltage $V_A$ is a combination of the biopotential at electrode A (for low frequencies) and of the impedance voltage drop (at high frequency). As noted above, the unit of electrodes A and a can be duplicated and connected to the same wire (101). A multi-electrode biopotential and impedance measuring device is therefore easily obtained.

The high frequency sine wave current injection can be modulated (for example with a square wave changing the amplitude of the sine wave every other millisecond). In this case, a circuit like the one depicted in FIG. 27 allows the synchronisation of both units by observing the voltages $U_1$ and $U_2$ that are available across impedances (200) and (201). These impedances (for instance a resistance or a capacitance) are on the same current loop and therefore the voltage across one of them is dependent on the voltage measured at the other. Additional units, connected to the same wire (101) and with their current source disabled, may be synchronized by observing their corresponding voltage $V_A$ at the impedance frequency.

The voltages $U_1$ and $U_2$ may also be used to measure the injected current with high accuracy. This feature may be useful in practice, because the current source can be imperfect (e.g., with relatively low internal impedance).

Figure 28:
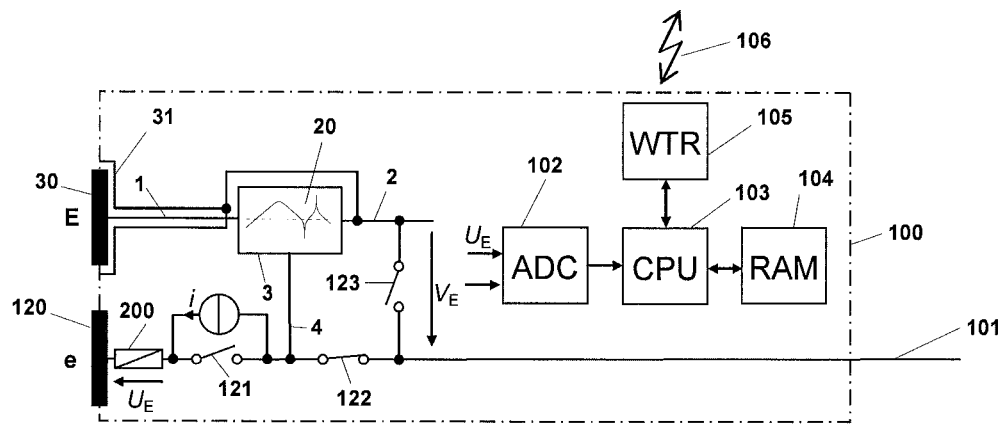

FIG. 28 depicts the combined generic unit for another one-wire biopotential and impedance measurements device.

Figure 22:
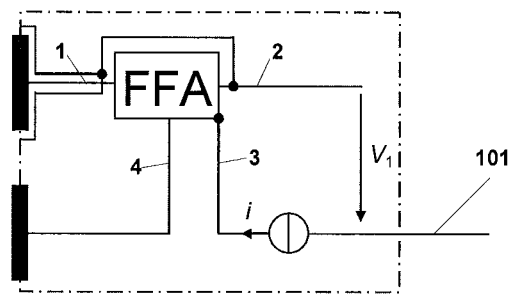
FIG. 22 shows an embodiment of the current source in the measuring unit different from the one shown in FIG. 21.
Figure 29:
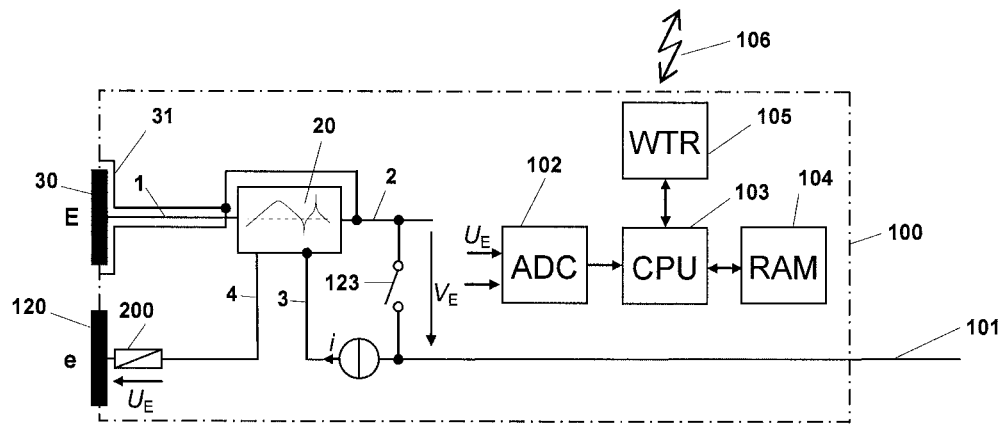

FIG. 29 shows an alternative combined generic unit for biopotential and impedance measurements based on the principle of FIG. 22.

Figure 30:
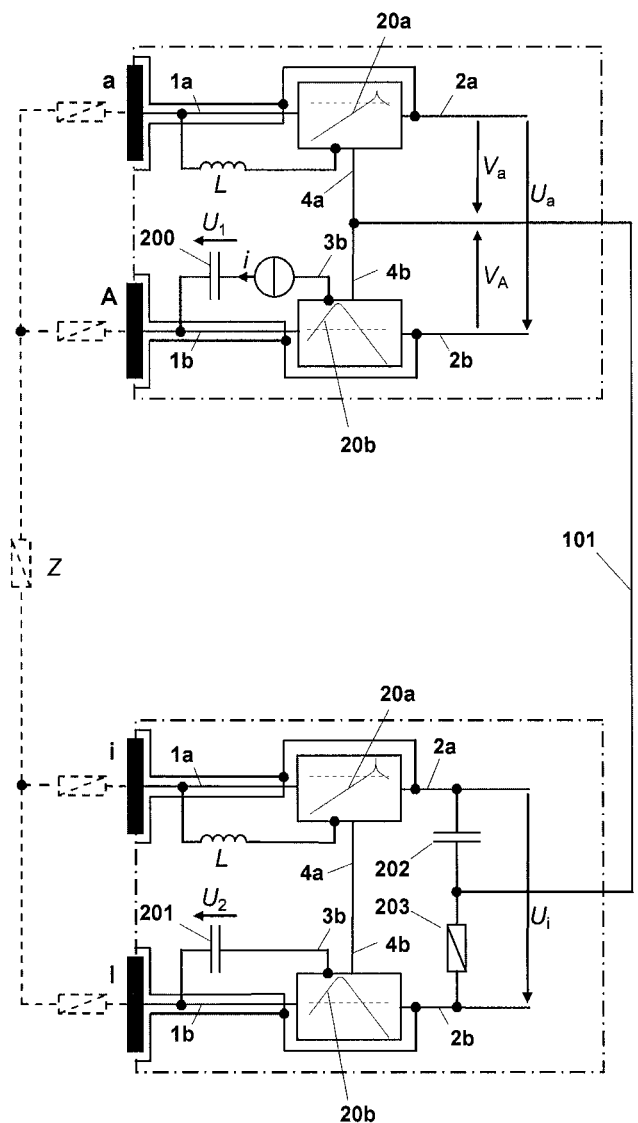
FIGS. 30 to 33 show embodiments for a one-wire measuring device in a configuration for biopotential and impedance measurements with contact impedance feature.

FIG. 30 depicts another one-wire combined biopotential and impedance measurements device. For biopotential measurements, the electrode I is used for sensing, while the electrode i is used as a guard electrode. The roles are reversed for impedance measurements. This circuit is more complex than the previous one. However, the injected current flows through the biopotential electrode. By measuring the voltages $U_a$ and $U_i$, the contact impedance of the electrodes A and I can be calculated. This information may be useful to reject motion artefacts in the biopotential measurement. Moreover, the contact impedance is appreciable information to assess the quality of electrode placement.

The measurement of voltages $U_1$ and $U_2$ may also be performed with wire (2b) instead of wire (1b). In this way, the input impedance at wire (1b) can be kept maximal without having to be altered by an additional measurement amplifier.

At biopotential frequencies, the inductance L and the transfer function (20a) results in a shortcut between (1a) and (4a). At the same time, the transfer function (20b) makes the capacitance (200) virtually absent. For these frequencies, the capacitance (202) and the impedance (203)—which is for instance a resistance or an inductance—make the external wire (101) virtually connected to (2b). At the impedance frequency, the inductance L can be seen as an open circuit, while the impedance of the capacitance (200) becomes low, and the external wire (101) is virtually connected to (2a).

The inductance L is actually in parallel with the input impedance of operational amplifier (8). As this impedance is essentially capacitive, it is advantageous to choose the inductance L so that the resulting resonant circuit presents an impedance theoretically infinite at the impedance frequency.

Figure 31:
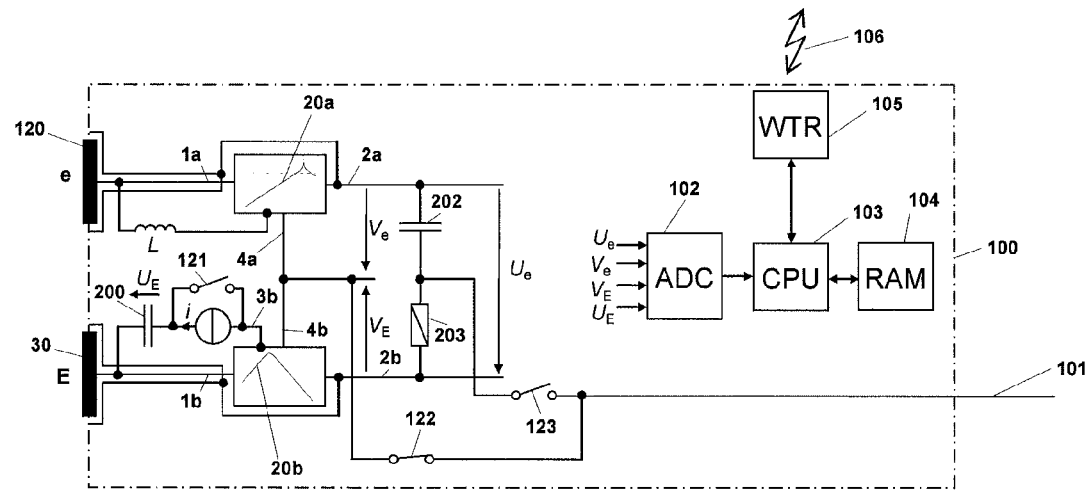

FIG. 31 depicts the combined generic unit for biopotential and impedance measurements with the contact impedance feature.

Figure 32:
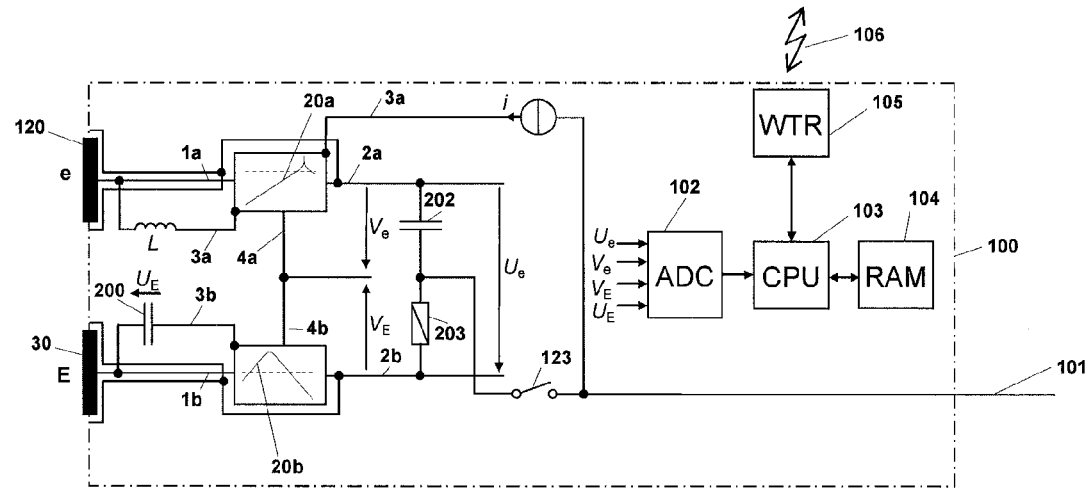

FIG. 32 depicts another combined generic unit for biopotential and impedance measurements with contact impedance feature.

Figure 33:
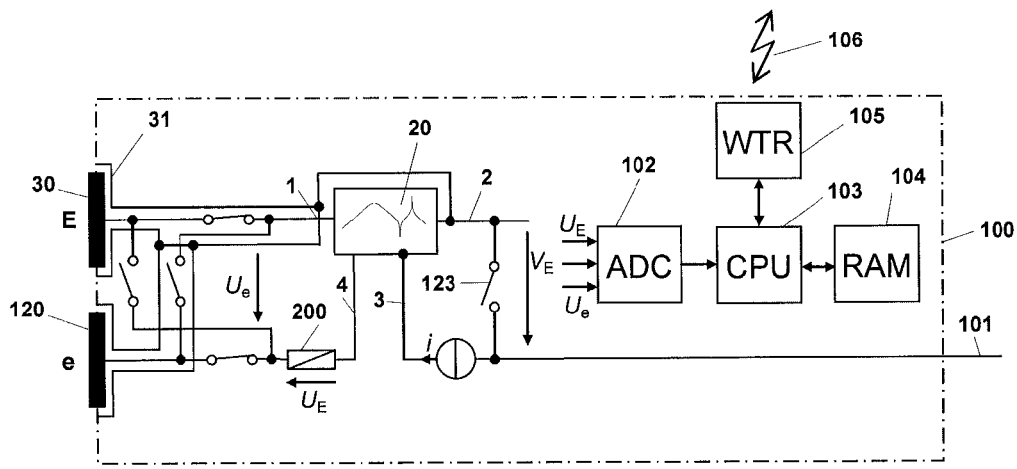

There is another circuit shown in FIG. 33 allowing measuring the contact impedance based on a temporal multiplexing instead of the frequency multiplexing shown above.

Switches are used to alternatively commute the role of the electrodes E and e. This circuit has the advantage of requiring only one floating front-end amplifier, but the price is a more complex logic and four extra switches are needed.

In an embodiment, the CPU (103) can numerically process the computation of impedance magnitude and phase (or alternatively the real and imaginary projections) if the sampling rate is high enough. Alternatively, this processing can also be performed before the ADC (102) by some analogue electronics (demodulation).

Figure 34:
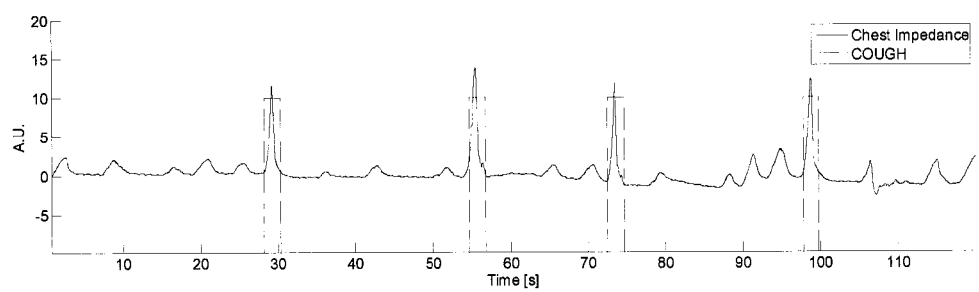
FIGS. 34 and 35 show, at rest (FIG. 34) and during walk (FIG. 35), the superiority of electrical chest impedance signals to tidal volume signals for the effective non-supervised assessment of cough.
Figure 34:
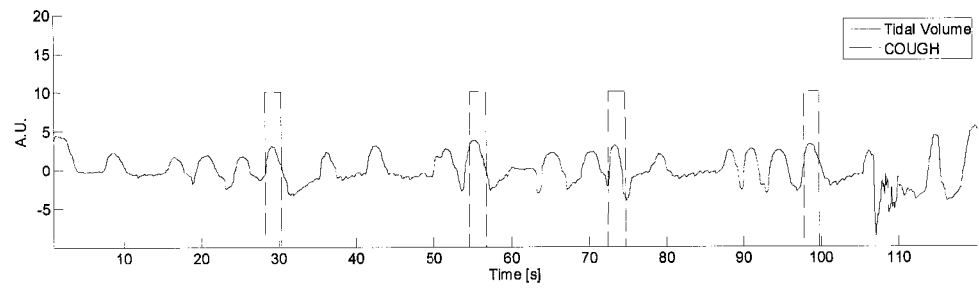
Figure 35:
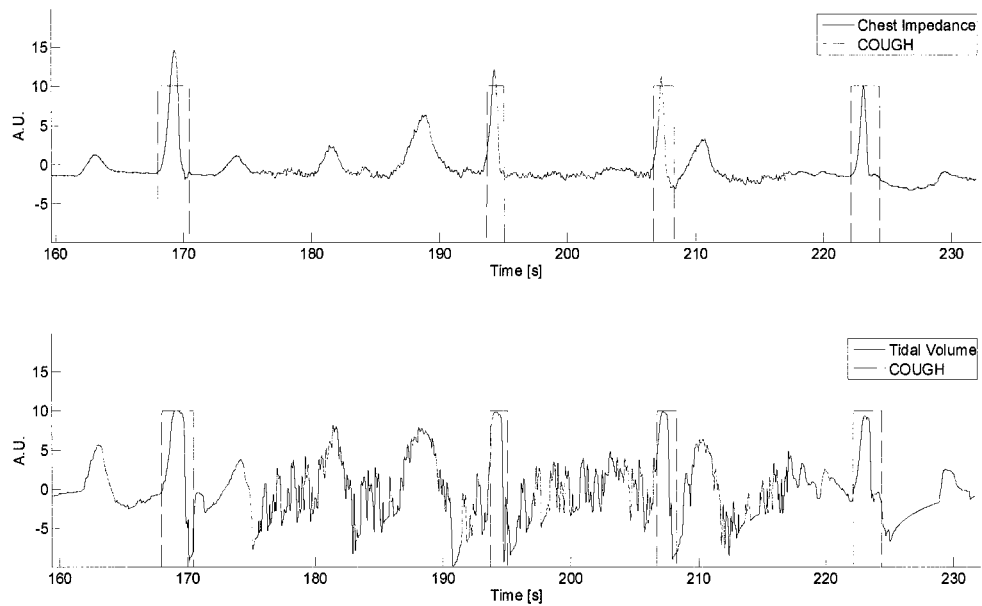

In another embodiment, the invented one-wire measuring device is provided with means for non-supervised assessment of cough dealing with impedance measurement. The proposed method differs from the prior art, because solely the chest impedance is processed in order to detect and classify cough events. FIG. 34 depicts tidal volume and chest electrical impedances during a non-motion period. FIG. 35 depicts tidal volume and chest electrical impedances during a walking period. One can notice the advantages of using chest electrical impedance instead of tidal volume on the robust detection of cough.

The invention claimed is:

1. A floating front-end amplifier comprising:
   a. an input, an output, an internal ground, and an external ground,
   b. a follower,
   c. a negative floating power supply and a positive floating power supply,
   d. a feedback filter, and
   e. a controlled voltage source,
with
   a. the voltage between said output and said internal ground being filtered by said feedback filter with the resulting signal driving said controlled voltage source,
   b. said controlled voltage source defining the potential of said external ground with respect to the potential of said internal ground,
   c. said input being connected to the input of said follower,
   d. said output being connected to the output of said follower,
   e. said follower being powered by said negative and positive floating power supplies, and
   f. said internal ground being connected to the ground of both said floating power supplies.

2. The floating front-end amplifier of claim 1, wherein said feedback filter drives said control voltage in such a way that at least at one frequency the feedback filter input is kept close to zero.

3. The floating front-end amplifier of claim 1, wherein said control voltage is built with an operational amplifier
   a. powered by said floating power supplies, and
   b. with its output connected to said external ground.

4. The floating front-end amplifier of claim 2, wherein said control voltage is built with an operational amplifier
   a. powered by said floating power supplies, and
   b. with its output connected to said external ground.

5. The floating front-end amplifier of claim 1, wherein said control voltage is built with a follower
   a. powered by power supplies connected to said external ground, and
   b. with its output connected to said internal ground.

6. The floating front-end amplifier of claim 2, wherein said control voltage is built with a follower
   a. powered by power supplies connected to said external ground, and
   b. with its output connected to said internal ground.

7. The floating front-end amplifier according to claim 1, wherein said floating power supplies are batteries.

8. The floating front-end amplifier according to claim 1, wherein said floating power supplies result from galvanically isolated DC/DC converters powered by its own power supply.

9. The floating front-end amplifier according to claim 1, including a shield enveloping all components of said floating front-end amplifier—except for some opening needed for connections with the outside—said shield being connected to said internal ground or to said output.

10. The floating front-end amplifier according to claim 1, including a shield enveloping that is electrically connected to said input—except its end(s) (for instance the active surface of an electrode)—said shield being connected to said internal ground or to said output.

11. The floating front-end amplifier according to claim 1, including a circuit managing the DC polarization of said follower, said circuit being connected to said input and to said internal ground and possibly to said output, and wherein said feedback filter has a magnitude zero for frequency zero.

12. The floating front-end amplifier according to claim 1, including an overvoltage protection circuit, one end being connected to said input and the other end to said output or to said internal ground.

13. A one-wire measuring device for biopotential and/or impedance measurements of a body comprising at least two units connected to the same external wire, with always one of these units taking the
function of a reference unit with
   a. a reference electrode,
   b. a guard electrode, and
   c. a floating front-end amplifier according to claim 1
with
   a. said reference electrode being connected to said input of said floating front-end amplifier,
   b. said guard electrode being connected to said external ground of said floating front-end amplifier,
   c. said external wire being connected to said output or said internal ground of said floating front-end amplifier, and
   d. possible means to measure the current flowing through said guard electrode for synchronization purposes between units,
the other units taking the function of measuring unit
   a. at least one of them with one biopotential and/or impedance electrode and measuring means of the voltage between the potentials of said biopotential and/or impedance electrode and said external wire, as well as signal processing means to extract from this voltage the biopotential and/or body impedance and/or synchronization information,
   b. at least one of them with recording and/or display and/or transmission means of the measured biopotential and/or body impedance and/or synchronization information, and
   c. for said impedance measurements or said synchronization purposes between units, at least one of them with a current injection electrode with means to circulate a current through said injection electrode, said body, said guard electrode and said external wire, said current being, if needed, modulated in such a way that its effects on the measured body impedance and/or on said means to measure the current flowing through said guard electrode can be extracted from the combined effects of other measuring unit current or biopotentials.

14. The one-wire measuring device of claim 13, wherein at least one of the units taking the function of measuring unit comprises a floating front-end amplifier with a. said input of said floating front-end amplifier being connected to the biopotential/impedance electrode,
b. said external ground of said floating front-end amplifier being connected to said external wire, and
c. for said impedance measurements or said synchronization purposes between units, a current source between said external ground and said current injection electrode as said means to circulate a current through said injection electrode, said body, said guard electrode and said external wire.

15. The one-wire measuring device of claim 13, wherein at least one of the units taking the function of measuring unit comprises a floating front-end amplifier with
a. said input of said floating front-end amplifier being connected to the biopotential/impedance electrode,
b. said external ground of said floating front-end amplifier being connected to said current injection electrode, and
c. for said impedance measurements or said synchronization purposes between units, a current source between said internal ground and said external wire as said means to circulate a current through said injection electrode, said body, said guard electrode and said external wire.

16. The one-wire measuring device of claim 13, wherein at least two units exchange, at start-up or during operation, the function of reference and measuring units, the reference unit possibly taking advantage to resynchronize with the other units.

17. The one-wire measuring device of claim 14, wherein at least two units exchange, at start-up or during operation, the function of reference and measuring units, the reference unit possibly taking advantage to resynchronize with the other units.

18. The one-wire measuring device of claim 15, wherein at least two units exchange, at start-up or during operation, the function of reference and measuring units, the reference unit possibly taking advantage to resynchronize with the other units.

19. The one-wire measuring device according to claim 13, wherein only one of the measuring unit, in turn, injects a current at a given time, the other being turned off (current equal to zero).

20. The one-wire measuring device according to claim 14, wherein only one of the measuring unit, in turn, injects a current at a given time, the other being turned off (current equal to zero).

21. The one-wire measuring device according to claim 15, wherein only one of the measuring unit, in turn, injects a current at a given time, the other being turned off (current equal to zero).

22. The one-wire measuring device according to claim 16, wherein only one of the measuring unit, in turn, injects a current at a given time, the other being turned off (current equal to zero).

23. The one-wire measuring device according to claim 13, characterized in that each measuring unit injects a current modulated by a different carrier.

24. The one-wire measuring device according to claim 13, wherein at least one measuring unit exchanges said biopotential/impedance electrode with said current injection electrode for impedance measurement so that the measurement of the voltage between both electrodes allows the computation of the contact impedance of the biopotential electrode.

25. The one-wire measuring device according to claim 13, wherein the reference unit exchanges said reference electrode with said guard electrode for impedance measurement so that the measurement of the voltage between both electrodes allows the computation of the contact impedance of the reference electrode.

26. The one-wire measuring device of claim 24, wherein said exchange is performed by controlled switches commuting in turn to both configurations so that biopotential, body impedance or/and contact impedance can be alternatively measured.

27. The one-wire measuring device of claim 25, wherein said exchange is performed by controlled switches commuting in turn to both configurations so that biopotential, body impedance or/and contact impedance can be alternatively measured.

28. The one-wire measuring device of claim 24, wherein said exchange is performed by electrical filters as a function of the frequency ranges occupied by the biopotential and by the modulated current use for body or/and contact impedance measurement.

29. The one-wire measuring device of claim 25, wherein said exchange is performed by electrical filters as a function of the frequency ranges occupied by the biopotential and by the modulated current use for body or/and contact impedance measurement.

30. The one-wire measuring device according to claim 13, comprising means for non-supervised assessing of cough with solely chest impedance measurements.

* * * * *